US006291684B1

(12) United States Patent
Borzilleri et al.

(10) Patent No.: US 6,291,684 B1
(45) Date of Patent: *Sep. 18, 2001

(54) PROCESS FOR THE PREPARATION OF AZIRIDINYL EPOTHILONES FROM OXIRANYL EPOTHILONES

(75) Inventors: Robert M. Borzilleri, New Hope, PA (US); Soong-Hoon Kim, Lawrenceville, NJ (US); Alicia Regueiro-Ren, Plainsboro, NJ (US); Gregory D. Vite, Titusville, NJ (US)

(73) Assignee: Bristol-Myers Squibb Company, Princeton, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/528,230

(22) Filed: Mar. 17, 2000

Related U.S. Application Data

(60) Provisional application No. 60/126,936, filed on Mar. 29, 1999.

(51) Int. Cl.$^7$ ...................... C07D 203/26; C07D 313/00; C07F 7/02

(52) U.S. Cl. ........................... 548/961; 549/214; 549/271

(58) Field of Search ................................... 549/214, 271; 548/961

(56) References Cited

FOREIGN PATENT DOCUMENTS

| | | |
|---|---|---|
| 4138042.8 | 5/1993 | (DE) . |
| 19542986 | 5/1997 | (DE) . |
| 19639456 | 5/1997 | (DE) . |
| 19636343 | 3/1998 | (DE) . |
| 19645361 | 4/1998 | (DE) . |
| 19645362 | 4/1998 | (DE) . |
| 19647580 | 5/1998 | (DE) . |
| 19701758 | 7/1998 | (DE) . |
| 19707505 | 9/1998 | (DE) . |
| 19713970 | 10/1998 | (DE) . |
| 19720312 | 11/1998 | (DE) . |
| 19821954 | 11/1998 | (DE) . |
| 19726627 | 12/1998 | (DE) . |
| 879 605 | 11/1998 | (EP) . |
| 93/10121 | 5/1993 | (WO) . |
| 97/19086 | 5/1997 | (WO) . |
| 98/08849 | 3/1998 | (WO) . |
| 98/22461 | 5/1998 | (WO) . |
| 98/24427 | 6/1998 | (WO) . |
| 98/25929 | 6/1998 | (WO) . |
| 98/38192 | 9/1998 | (WO) . |
| 98/47891 | 10/1998 | (WO) . |
| 99/01124 | 1/1999 | (WO) . |
| 99/03848 | 1/1999 | (WO) . |
| 99/07692 | 2/1999 | (WO) . |

OTHER PUBLICATIONS

Vite, G. et al 'Synthesis and cytotoxicity of 12, 13–modified epothilone derivatives for use in treatment of tumors or other hyperproliferative cellular disease' CA 131:310502, 1999.*

Balog, A., et al., "Total Synthesis of (–)–Epothilone A", *Angew. Chem. Int. Ed. Engl.,* vol. 35, No. 23/24, 2801–2803 (1996).

Bertini, F., et al., "Alkenes from Epoxides by Reductive Elimination with Magnesium Bromide–Magnesium Amalgam", *Chem. Commun.,* 144 (1970).

Bollag, D.M., et al., "Epothilones, A New Class of Microtubule–stabilizing Agents with a Taxol–like Mechanism of Action", *Cancer Res.* 55, No. 11, 2325–2333 (1995).

Fujiwara, Y., et al., "Reductive Coupling of Carbonyl Compounds to Olefins by Tungsten Hexachloride–Lithium Aluminum Hydride and Some Tungsten and Molybdenum Carbonyls", *J. Org. Chem.,* vol. 43, No. 12, 2477–2479 (1978).

Fujisawa, T., et al., "Deoxygenation of Epoxides to Olefins with FeCl$_3$–n–BuLi System", *Chem. Lett.,* 883–886 (1974).

Gladysz, J. A. et al., "Deoxygenation of Epoxides by Metal Atom Cocondensation", *J. Org. Chem.,* vol. 41, No. 22, 3647–3648 (1976).

Hofle, G., et al., "Epothilone A and B –Novel 16–Membered Macrolides with Cytotoxic Activity: Isolation, Crystal Structure, and Conformation in Solution", *Angew. Chem. Int. Ed. Engl.,* vol. 35, No. 13/14, 1567–1569 (1996).

Hofle, G., et al., "N–Oxidation of Epothilone A–C and O–Acyl Rearrangement to C–19 and C–21 –Substituted Epothilones", *Angew. Cem. Int. Ed.,* vol. 38, No. 13/14, 1971–1974 (1999).

Inokuchi,T., et al., "Opening of Epoxides to Olefins or Halohydrins with Vanadium(II)–Tetrahydrofuran or Vanadium(III)–Tetrahydrofuran Complexes", *Synlett,* No. 6, 510–512 (1992).

Kowalski. R. J., et al., "Activities of the Microtubule–stabilizing Agents Epothilones A and B with Purified Tubulin and in Cells Resistant to Paclitaxel (Taxol®)" *J. Biol. Chem.,* vol. 272, No. 4, 2534–2541 (1997).

Kupchan, S. M., et al., "Reductive Elimination of Epoxides to Olefins with Zinc–Copper Couple", *J. Org. Chem.,* vol. 36, No. 9, 1187–1190 (1971).

Martin, M. G., et al., "Epoxides as Alkene Protecting Groups. A Mild and Efficient Deoxygenation", *Tetrahedron Letters,* vol. 25, No. 3, 251–254 (1984).

McMurry, J. E., et al., "Reduction of Epoxides to Olefins with Low Valent Titanium", *J. Org. Chem.,* vol. 40, No. 17, 2555–2556 (1975).

McMurry, J.E., et al., "Some Deoxygenation Reactions with Low–Valent Titanium (TiCl$_3$/LiAlH$_4$)", *J. Org. Chem.,* vol. 43, No. 17, 3249–3254 (1978).

(List continued on next page.)

*Primary Examiner*—Amelia Owens
(74) *Attorney, Agent, or Firm*—Rena Patel; Joan E. Switzer

(57) ABSTRACT

The present invention relates to a stereospecific process to produce aziridinyl epothilones from oxiranyl epothilones and the intermediates derived therein.

10 Claims, No Drawings

OTHER PUBLICATIONS

Meng, D., et al., "Remote Effects in Macrolide Formation Through Ring–Forming Olefin Metathesis: An Application to the Synthesis of Fully Active Epothilone Congeners", *J. Am. Chem. Soc.*, vol. 119, No. 11, 2733–2734 (1997).

Nicolaou, K. C., et al., "An Approach to Epothilones Based on Olefin Metathesis", *Angew. Chem. Int. Ed. Engl.*, vol. 35, No. 20, 2399–2401 (1996).

Nicolaou, K. C. et al., "Total Synthesis of Epothilone A: The Macrolactonization Approach", *Angew. Chem. Int. Ed. Engl.*, vol.36, No. 5, 525–527 (1997).

Nicolaou, K. C., et al., "Designed Epothilones: Combinatorial Synthesis, Tubulin Assembly Properties, and Cytotoxic Action against Taxol–Resistant Tumor Cells", *Angew. Chem. Int. Ed. Engl.*, vol. 36, No. 19, 2097–2103 (1997).

Nicolaou, K.C. et al., "The Olefin Metathesis Approach to Epothilone A and Its Analogues", *J. Am. Chem Soc.*, vol. 119, No. 34, 7960–7973 (1997).

Nicolaou, K. C., et al., "Total Syntheses of Epothilones A and B via a Macrolactonization–Based Strategy", *J. Am. Chem. Soc.*, vol. 119, No. 34, 7974–7991 (1997).

Nicolaou, K. C., et al., "Synthesis of Epothilones A and B in Solid and Solution Phase", *Nature*, vol. 387, 268–272 (1997).

Nicolaou, K. C., et al., "Synthesis of Epothilones A and B in Solid and Solution Phase"(Correction to *Nature* 387, 268–272 (1997)), Nature, 390, 100 (1997).

Raucher, S., et al., "Total Synthesis of (+)–Dihydrocostunolide via Tandem Cope–Claisen Rearrangement", *J. Org. Chem.*, vol. 51, No. 26, 5503–5505 (1986).

Sato, M, et al., "Reduction of Organic Compounds with Low–Valent Niobium ($NbCl_5$/$NaAlH_4$)", *Chem. Letters*, 157–160 (1982).

Schinzer, D., et al., "Total Synthesis of (–)–Epothilone A", *Angew. Chem. Int. Ed. Engl.*, vol. 36, No. 5, 523–524 (1997).

Schobert, R., et al., "Reduction and Isomerization of Oxiranes and α–Diazoketones by Various Early Transition Metallocenes", *Synlett*, vol. 8, 465–466 (1990).

Sharpless, K. B., et al., "Lower Valent Tungsten Halides. A New Class of Reagents for Deoxygenation of Organic Molecules", *J. Amer. Chem. Soc.*, vol. 94, No. 18, 6538–6540 (1972).

Su, D.–S., et al., "Total Synthesis of (–)–Epothilone B: An Extension of the Suzuki Coupling Method and Insights into Structure–Activity Relationships of the Epothilones", *Angew. Chem. Int. Ed. Engl.*, vol. 36, No. 7, 757–759 (1997).

Su, D.–S., et al., "Structure–Activity Relationships of the Epothilones and the First In Vivo Comparison with Paclitaxel", *Angew. Chem. Int. ed. Engl.*, vol. 36, No. 19, 2093–2096 (1997).

Victory, S. F., et al., "Relative Stereochemistry and Solution Conformation of the Novel Paclitaxel–Like Antimitotic Agent Epothilone A", *Bioorg. Med. Chem. Letts.*, vol. 6., No. 7, 893–898 (1996).

Winkler, J. D., et al., "A Model For The Taxol (Paclitaxel)/Epothilone Pharmacophore", *Bioorg. Med. Chem. Letts.*, vol. 6, No. 24, 2963–2966 (1996).

Yang, Z., et al., "Total Synthesis of Epothilone A: The Olefin Metathesis Approach", *Angew. Chem. Int. Ed. Engl.*, vol. 36, No. 1 / 2, 166–168 (1997).

Bollag, D., et al., "Epothilone, A New Structural Class of Microtubule Stabilizer", Abstract, *Proc. Am. Assoc. Cancer Res.*, vol. 36, 86 Meet. 454 (1995).

Bollag, D., "Epothilones: Novel Microtubule–Stabilising Agents", *Expert Opin. Invest. Drugs*, vol. 6,No. 7, 867–873 (1997).

Bertinato, P., et al., "Studies Toward a Synthesis of Epothilone A: Stereocontrolled Assembly of the Acyl Region and Models for Macrocyclization", J. Org. Chem., vol. 61, No. 23, 8000–8001 (1996).

*Chemical & Engineering News*, "Epothilone Epiphany: Total Syntheses", vol. 74, No. 52, 24–26 (1996).

*Chemical & Engineering News*, "First Total Synthesis of Epothilone B", vol. 75, No. 13, 23 (1997).

*Chemical & Engineering News*, "Solid–Phase Epothilone Synthesis Used to Create Analog Library", vol. 75, No. 20, 33 (1997).

Claus, E., et al., "Synthesis of the C1–C9 Segment of Epothilons", *Tetrahedron Lett.*, vol. 38, No. 8, 1359–1362 (1997).

De Brabander, J., et al., "Towards a Synthesis of Epothilone A: Rapid Assembly of the C1–C6 and C7–C12 Fragments", *Synlett*, vol. 7, 824–826 (1997).

Gabriel, T. and Wessjohann, L., "The Chromium–Reformatsky Reaction: Asymmetric Synthesis of the Aldol Fragment of the Cytotoxic Epothilons from 3–(2–Bromoacyl)–2–Oxazolidinones", *Tetrahedron Lett.*, vol. 38, No. 8, 1363–1366 (1997).

Gerth, K., et al., "Epothilons A and B: Antifungal and Cytotoxic Compounds from *Sorangiusm cellulosum* (Myxobacteria) Production Physico–chemical and Biological Properties", *J. Antibiotics*, vol. 49, No. 6, 560–563 (1996).

Marshall, A., "Total Synthesis of Epothilone", *Nature Biotechnology*, vol. 15, No. 3, 205 (1997).

Meng, D., et al., "Studies Toward a Synthesis of Epothilone A: Use of Hydropyran Templates for the Management of Acyclic Stereochemical Relationships", *J. Org. Chem.*, vol. 61, No. 23, 7998–7999 (1996).

Meng, D., et al., "Total Syntheses of Epothilones A and B", *J. Am. Chem. Soc.*, vol. 119, No. 42, 10073–10092 (1997).

Mensching, S. and Kalesse, M., "Generation of Thiazoles by Column Dehydrogenation of Thiazolidines with $MnO_2$ ",*J. Prakt. Chem.*, vol. 339, No. 1, 96–97 (1997).

Mulzer, J. and Mantoulidis, A., "Synthesis of the C(1)–C(9) Segment of the Cytotoxic Macrolides Epothilon A and B", *Tetrahedron Lett.*, vol. 37, No. 51, 9179–9182 (1996).

Nicolaou, K., et al., "Chemistry, Biology and Medicine of Selected Tubulin Polymerizing Agents", *Pure Appl. Chem.*, vol. 71, No. 6, 989–997 (1999).

Nicolaou, K., et al., "Total Synthesis of Epothilone E and Related Sidechain Modified Analogues Via a Stille Coupling Based Strategy", *Bioorg. Med. Chem.*, vol. 7, No. 5, 665–697 (1999).

Schinzer, D., et al., "Studies Towards the Total Synthesis of Epothilones: Asymmetric Synthesis of the Key Fragments", *Chem. Eur. J.*, vol. 2, No. 22, 1477–1482 (1996).

Taylor, R. and Haley, J., "Towards the Synthesis of Epothilone A: Enantioselective Preparation of the Thiazole Sidechain and Macrocyclic Ring Closure", *Tetrahedron Lett.*, vol. 38, No. 12, 2061–2064 (1997).

Schinzer, D., et al., "Syntheses of (–)–Epothilone B", *Chem. Eur. J.*, vol. 5, No. 9, 2483–2491 (1999).

Schinzer, D., et al., "Syntheses of (–)–Epothilone A", *Chem. Eur. J.*, vol. 5, No. 9, 2492–2500 (1999).

Nicolaou, K. C., et al., "Synthesis and Biological Properties of C12, 13–Cyclopropylepothilone A and Related Epothilones", *Chemistry & Biology*, vol. 5, No. 7, 365–372 (1998).

* cited by examiner

PROCESS FOR THE PREPARATION OF AZIRIDINYL EPOTHILONES FROM OXIRANYL EPOTHILONES

This application claims priority from provisional U.S. application Ser. No. 60/126,936, filed Mar. 29, 1999, incorporated herein by reference in its entirety

FIELD OF THE INVENTION

The present invention relates to a stereospecific process for the preparation of epothilone derivatives and intermediates therefor.

BACKGROUND OF THE INVENTION

Epothilones are macrolide compounds which find utility in the pharmaceutical field. For example, Epothilones A and B having the structures:

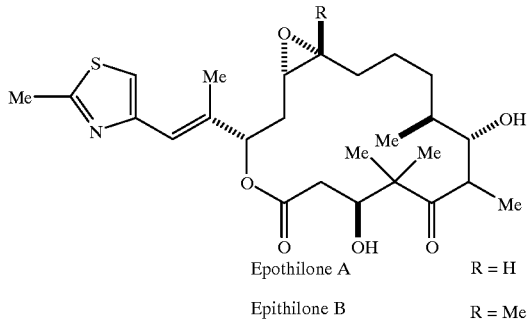

Epothilone A     R = H

Epithilone B     R = Me have been found to exert microtubule-stabilizing effects similar to paclitaxel (TAXOL®) and hence cytotoxic activity against rapidly proliferating cells, such as, tumor cells or other hyperproliferative cellular disease, see *Angew. Chem. Int. Ed. Engl.*, Vol. 35, No.13/14, 1567–1569 (1996).

Derivatives and analogs of Epothilones A and B have been synthesized and have been used to treat a variety of cancers and other abnormal proliferative diseases.

Such analogs are disclosed in Hofle et al., *Angew. Chem. Int. Ed. Engl.*, 35, No.13/14 (1996); WO93/10121 published May 27, 1993 and WO97/19086 published May 29, 1997; and Nicolaou et al., *Angew Chem. Int. Ed. Engl.*, Vol. 36, No. 19, 2097–2103 (1997); and Su et al., *Angew Chem. Int. Ed. Engl.*, Vol. 36, No. 19, 2093–2096 (1997).

For reasons of stability, it would be desirable to convert the epoxide moiety of Epothilones A and B to their corresponding aziridine form. However, conventional methods of affecting this conversion, such as the methods of R. Zamboni and J. Rokach, *Tetrahedron Letters*, 331–334 (1983); and Y. Ittah et al., *J. Org. Chem.*, 43, 4271–4273 (1978), result in a molecule having an opposing stereoconfiguration.

Applicants have now found a process for synthesizing epothilones that retains the stereoconfiguration of the starting material.

SUMMARY OF THE INVENTION

The present invention is a process for preparing stereospecific aziridinyl epothilones and the intermediates derived therein. The invention is directed to a process for preparing compounds of structure VI

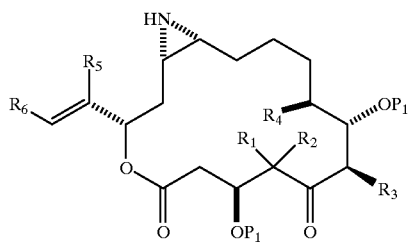

wherein:

$R_1$, $R_2$, $R_3$, $R_4$, $R_5$ are selected from the group H or alkyl and when $R_1$ and $R_2$ are alkyl can be joined to form a cycloalkyl;

$R_6$ is selected from the group consisting of H, alkyl, substituted alkyl, aryl, substituted aryl, cycloalkyl, or heterocyclo;

$R^7$ is selected from the group consisting of alkyl, substituted alkyl, aryl, or substituted aryl; and $P_1$ is selected from the group H, alkyl, substituted alkyl, alkanoyl, substituted alkanoyl, aroyl, substituted aroyl, trialkylsilyl, aryl dialkylsilyl, diaryl alkylsilyl, triarylsilyl;

which comprises:

(a) reacting a compound of structure I

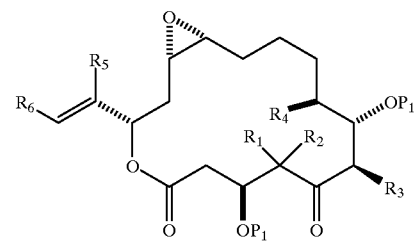

wherein $R_{1-6}$ and $P_1$ are defined as above with at least one metal halide salt to form structure II;

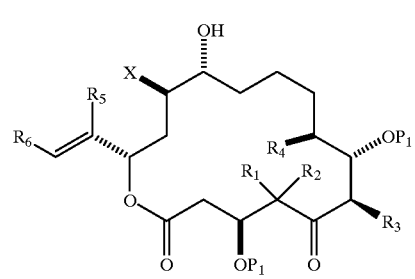

(b) reacting the product of (a) with at least one azide salt to form structure III;

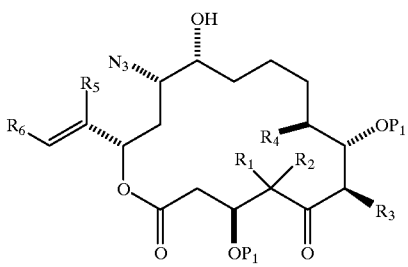

(c) conducting a Mitsunobu reaction with the product of (b) to form structure IV; X

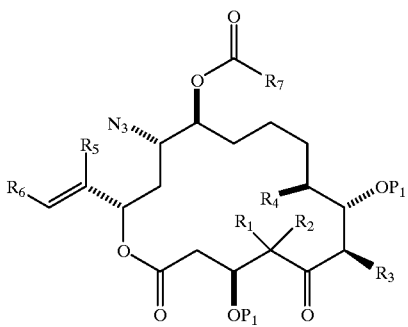

(d) cleaving the ester group of the product of (c) to form structure

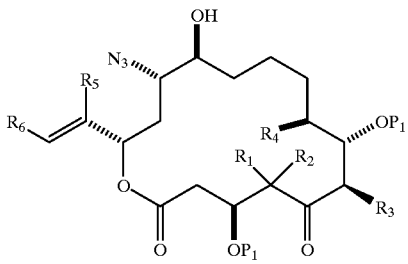

and (e) reducing and cyclizing the product of (d) with a reducing agent to form the stereospecific form of structure VI.

DETAILED DESCRIPTION OF THE INVENTION

Definitions

Listed below are definitions of various terms used to describe this invention. These definitions apply to the terms as they are used throughout this specification, unless otherwise limited in specific instances, either individually or as part of a larger group.

The term "pharmaceutically active agent" or "pharmaceutically active epothilone" refers to an epothilone that is pharmacologically active in treating cancer or other diseases described herein.

The term "alkyl" refers to optionally substituted, straight or branched chain saturated hydrocarbon groups of 1 to 20 carbon atoms, preferably 1 to 7 carbon atoms. The expression "lower alkyl" refers to optionally substituted alkyl groups of 1 to 4 carbon atoms.

The term "substituted alkyl" refers to an alkyl group substituted by, for example, one to four substituents, such as, halo, trifluoromethyl, trifluoromethoxy, hydroxy, alkoxy, cycloalkyloxy, heterocyclooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl, alkanoylamino, aroylamino, aralkanoylamino, substituted alkanoylamino, substituted arylamino, substituted aralkanoylamino, thiol, alkylthio, arylthijo, aralkylthio, cycloalkylthio, heterocyclothio, alkylthiono, arylthiono, aralkylthiono, alkylsulfonyl, arylsulfonyl, aralkylsulfonyl, sulfonamido (e.g. $SO_2NH_2$), substituted sulfonamido, nitro, cyano, carboxy, carbamyl (e.g. $CONH_2$), substituted carbamyl (e.g. CONH alkyl, CONH aryl, CONH aralkyl or cases where there are two substituents on the nitrogen selected from alkyl, aryl or aralkyl), alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Where noted above where the substituent is further substituted it will be with halogen, alkyl, alkoxy, aryl or aralkyl.

The term "aryl" refers to monocyclic or bicyclic aromatic hydrocarbon groups having 6 to 12 carbon atoms in the ring portion, such as phenyl, naphthyl, biphenyl and diphenyl groups, each of which may be optionally substituted.

The term "substituted aryl" refers to an aryl group substituted by, for example, one to four substituents such as alkyl; substituted alkyl, halo, trifluoromethoxy, trifluoromethyl, hydroxy, alkoxy, cycloalkyloxy, heterocyclooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by halo, hydroxy, alkyl, alkoxy, aryl, substituted aryl, substituted alkyl or aralkyl.

The term "aralkyl" refers to an aryl group bonded directly through an alkyl group, such as benzyl.

The term "substituted alkene" and "substituted alkenyl" refer to a moiety having a carbon to carbon double bond, which can be part of a ring system, with at least one substituent being a lower alkyl or substituted lower alkyl. Other substituents are as defined for substituted alkyl.

The term "cycloalkyl" refers to a optionally substituted, saturated cyclic hydrocarbon ring systems, preferably containing 1 to 3 rings and 3 to 7 carbons per ring which may be further fused with an unsaturated $C_3$–$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclo" refer to an optionally substituted, unsaturated, partially saturated, or fully saturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1, 1-dioxothienyl, dioxanyl, isothiazolidinyl, thietanyl, thiiranyl, riazinyl, and triazolyl, and the like.

Exemplary bicyclic heterocyclic groups include benzothiazolyl, benzoxazolyl, enzothienyl, quinuclidinyl, quinolinyl, quinolinyl-N-oxide, tetrahydroisoquinolinyl, isoquinolinyl, benzimidazolyl, benzopyranyl, indolizinyl, benzofliryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl groups as described above or one or more groups described above as alkyl substituents. Also included are smaller heterocyclos, such as, epoxides and aziridines.

The term "alkanoyl" refers to —C(O)-alkyl.

The term "substituted alkanoyl" refers to —C(O)-substituted alkyl.

The term "aroyl" refers to —C(O)-aryl.

The term "substituted aroyl" refers to —C(O)-substituted aryl.

The term "trialkylsilyl" refers to —Si(alkyl)$_3$.

The term "aryl dialkylsilyl" refers to —Si(alkyl)$_2$ (aryl).

The term "diaryl alkylsilyl" refers to —Si(aryl)$_2$ (alkyl).

The term "heteroatoms" shall include oxygen, sulfur and nitrogen.

The term "halogen" or "halo" refers to fluorine, chlorine, bromine and iodine.

The compounds of formula VI may form salts with alkali metals such as sodium, potassium and lithium, with alkaline earth metals such as calcium and magnesium, with organic bases such as dicyclohexylamine and tributylamine, with pyridine and amino acids such as arginine, lysine and the like. Such salts can be obtained, for example, by exchanging the carboxylic acid protons, if they contain a carboxylic acid, from compounds of formula VI with the desired ion in a medium in which the salt precipitates or in an aqueous medium followed by evaporation. Other salts can be formed as known to those skilled in the art.

The compounds of formula VI form salts with a variety of organic and inorganic acids. Such salts include those formed with hydrogen chloride, hydrogen bromide, methanesulfonic acid, hydroxyethanesulfonic acid, sulfiric acid, acetic acid, trifluoroacetic acid, maleic acid, benzenesulfonic acid, toluenesulfonic acid and various others (e.g. nitrates, phosphates, borates, tartrates, citrates, succinates, benzoates, ascorbates, salicylates and the like). Such salts are formed by reacting a compound of formula I through IV in an equivalent amount of the acid in a medium in which the salt precipitates or in an aqueous medium followed by evaporation.

In addition, zwitterions ("inner salts") can be formed and are included within the term salts as used herein.

Prodrugs and solvates of the compounds of formula VI are also contemplated herein. The term prodrug, as used herein, denotes a compound which, upon administration to a subject, undergoes chemical conversion by metabolic or chemical processes to yield a compound of formula I through IV, or a salt and/or solvate thereof. For example, compounds of formula I through IV may form a carboxylate ester moiety. The carboxylate esters are conveniently formed by esterifying any of the carboxylic acid functionalities found on the disclosed ring structure(s). Solvates of the compounds of formula I through IV are preferably hydrates.

Various forms of prodrugs are well known in the art. For examples of such prodrug delivery derivatives, see:

a) *Design of Prodrugs*, H. Bundgaard (editor), Elsevier (1985);

b) *Methods in Enzymology*, K. Widder et al. (editors), Academic Press, Vol. 42, 309–396 (1985);

c) *A Textbook of Drug Design and Development*, Krosgaard-Larsen and H. Bundgaard (editors), Chapter 5, "Design and Application of Prodrugs," 113–191 (1991);

d) H. Bundgaard, *Advanced Drug Delivery Reviews*, 8, 1–38 (1992);

e) H. Bundgaard, *J. of Pharm. Sciences*, 77, 285 (1988); and f) N. Kakeya et al., *Chem. Pharm. Bull.*, 32 692 (1984).

The compounds of the invention may exist as multiple optical, geometric, and stereoisomers. While the compounds shown herein are depicted for one optical orientation, included within the present invention are all isomers and mixtures thereof.

Use and Utility

The compounds of the invention are microtubule-stabilizing agents. They are thus useful in the treatment of a variety of cancers and other proliferative diseases including, but not limited to, the following;

carcinoma, including that of the bladder, breast, colon, kidney, liver, lung, ovary, pancreas, stomach, cervix, thyroid and skin; including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma;

hematopoietic tumors of myeloid lineage, including acute and chronic myelogenous leukemias and promyelocytic leukemia;

tumors of mesenchymal origin, including fibrosarcoma and rhabdomyoscarcoma;

other tumors, including melanoma, seminoma, tetratocarcinoma, neuroblastoma and glioma;

tumors of the central and peripheral nervous system, including astrocytoma, neuroblastoma, glioma, and schwannomas;

tumors of mesenchymal origin, including fibrosarcoma, rhabdomyoscaroma, and osteosarcoma; and other tumors, including melanoma, xenoderma pigmentosum, keratoactanthoma, seminoma, thyroid follicular cancer and teratocarcinoma.

Compounds of the invention will also inhibit angiogenesis, thereby affecting the growth of tumors and providing treatment of tumors and tumor-related disorders. Such anti-angiogenesis properties of the compounds of formula VI will also be useful in the treatment of other conditions responsive to anti-angiogenesis agents including, but not limited to, certain forms of blindness related to retinal vascularization, arthritis, especially inflammatory arthritis, multiple sclerosis, restinosis and psoriasis.

Compounds of the invention will induce or inhibit apoptosis, a physiological cell death process critical for normal development and homeostasis. Alterations of apoptotic pathways contribute to the pathogenesis of a variety of human diseases. Compounds of formula VI, as modulators of apoptosis, will be useful in the treatment of a variety of human diseases with aberrations in apoptosis including, but not limited to, cancer and precancerous lesions, immune response related diseases, viral infections, degenerative diseases of the musculoskeletal system and kidney disease.

Without wishing to be bound to any mechanism or morphology, compounds of the invention may also be used to treat conditions other than cancer or other proliferative diseases. Such conditions include, but are not limited to viral infections such as herpesvirus, poxvirus, Epstein-Barr virus, Sindbis virus and adenovirus; autoimmune diseases such as systemic lupus erythematosus, immune mediated glomerulonephritis, rheumatoid arthritis, psoriasis, inflammatory bowel diseases and autoimmune diabetes mellitus; neurodegenerative disorders such as Alzheimer's disease, AIDS-related dementia, Parkinson's disease, amyotrophic lateral sclerosis, retinitis pigmentosa, spinal muscular atrophy and cerebellar degeneration; AIDS; myelodysplastic syndromes; aplastic anemia; ischemic injury associated myocardial infarctions; stroke and reperfusion injury; restenosis; arrhythmia; atherosclerosis; toxin-induced or alcohol induced liver diseases; hematological diseases such as chronic anemia and aplastic anemia; degenerative diseases of the musculoskeletal system such as osteoporosis and arthritis; aspirin-sensitive rhinosinusitis; cystic fibrosis; multiple sclerosis; kidney diseases; and cancer pain.

The present invention thus provides a method of treating a subject, preferably mammals and especially humans, in need of treatment for any of the aforementioned conditions, especially cancer or other proliferative diseases, comprising the step of administering to a subject in need thereof of at least one compound of formula I and II in an amount effective therefor. Other therapeutic agents such as those described below may be employed with the inventive compounds in the present method. In the method of the present invention, such other therapeutic agent(s) may be administered prior to, simultaneously with or following the administration of the compound(s) of the present invention.

The effective amount of a compound of the present invention may be determined by one of ordinary skill in the art, and includes exemplary dosage amounts or a human of from about 0.05 to 200 mg/kg/day, which may be administered in a single dose or in the form of individual divided doses, such as from 1 to 4 times per day. Preferably the compounds are administered in a dosage of less than 100 mg/kg/day, in a single dose or in 2 to 4 divided doses. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to the aforementioned disorders.

The present invention also provides a pharmaceutical composition comprising at least one of the compounds of formula VI capable of treating cancer or other proliferative diseases in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation or called for by accepted pharmaceutical practice.

The compounds of formula VI may be administered by any suitable means, for example, orally, such as in the form of tablets, capsules, granules or powders; sublingually; bucally; parenterally, such as by subcutaneous, intravenous, intramuscular, or intrastemal injection or infusion techniques (e.g., as sterile injectable aqueous or non-aqueous solutions or suspensions); nasally, such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally. For example, the active substance can be utilized in a composition such as a tablet, capsule, solution or suspension containing about 5 to about 500 mg per unit dosage of a compount or mixture of compounds of formula VI or in a topical form (0.01 to 5% by weight compound of formula VI, one to five treatments per day). They may be compounded in a conventional manner with a physiologically acceptable vehicle or carrier, excipient, binder, preservative, stabilizer, flavor, etc., or with a topical carrier.

The compounds of formula VI can also be formulated in compositions such as sterile solutions or suspensions for parenteral administration. About 0.1 to 500 mg of a compound of formula VI may be compounded with a physiologically acceptable vehicle, carrier, excipient, binder preservative, stabilizer, etc., in a unit dosage form as called for by accepted pharmaceutical practice. The amount of active sustance in these compositions or preparations is preferably such that a suitable dosage in the range indicated is obtained.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art.

Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g. Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parentally acceptable diluents or solvents, such as cremophor, mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperature, but liquify and/or dissolve in the rectal cavity to release the drug.

Exemplary compositions for topical administration include a topical carrier such as Plastibase (mineral oil gelled with polyethylene). For example, the compounds of the invention may be administered topically to treat plaques associated with psoriasis and as such may be formulated as a cream or ointment.

The compounds of the invention may be administered either alone or in combination with other anti-cancer and cytotoxic agents and treatments useful in the treatment of cancer or other proliferative diseases. Especially useful are anti-cancer and cytotoxic drug combinations wherein the second drug chosen acts in a different manner or different phase of the cell cycle, e.g. S phase, than the present compounds of formula I and II which exert their effects at the $G_2$-M phase. Example classes of anti-cancer and cytotoxic agents include, but are not limited to: alkylating agents, such as nitorgen mustards, alkyl sulfonates, nitrosoureas, ethylenimines, and triazenes; antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids, estrogens/antiestrogens, androgens/antiandrogens, progestins, and luteinizing hormone-releasing hormone anatagonists, octreotide acetate; microtubule-disruptor agents, such as ecteinascidins or their analogs and derivatives; microtubule-stabilizing agents such as paclitaxel (Taxol®), docetaxel (Taxotere®), and epothilones A–F or their analogs or derivatives; plant-derived products, such as vinca alkaloids, epipodophyllotoxins, taxanes; and topoisomerase inhibitors; prenyl-protein transferase inhibitors; and miscellaneous agents such as, hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators, and monoclonal antibodies. The compounds of the invention may also be used in conjunction with radiation therapy.

Representative examples of these classes of anti-cancer and cytotoxic agents include, but are not limited to, mechlorethamine hydrochlordie, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred members of these classes include, but are not limited to paclitaxel, cisplatin, carboplatin, doxorubicin, carminomycin, daunorubicin, aminopterin, methotrexate, methopterin, mitomycin C, ecteinascidin 743, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine, and leurosine.

Examples of anti-cancer and other cytotoxic agents include the following:

epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO99/27890, and WO 99/28324; WO 99/43653, WO 99/54330, WO 99/54318, WO 99/54319, WO 99/65913, WO 99/67252, WO 99/67253, and WO 00/00485; cyclin dependent kinase inhibitors as found in WO 99124416; and prenyl-protein transferase inhibitors as found in WO 97/30992 and WO 98/54966.

The combinations of the present invention may also be formulated or co-administered with other therapeutic agents that are selected for their particular usefulness in administering therapies associates with the aforementioned conditions. For example, the compounds of the invention may be formulated with agents to prevent nausea, hypersensitivity, and gastric irritation, such as antiemetics, and $H_1$ and $H_2$ antihistaminics.

The above therapeutic agents, when employed in combination with the compounds of the present invention, may be used in those amounts indicated in the Physicians' Desk Reference (PDR) or as otherwise determined by one of ordinary skill in the art.

Methods of Preparation

Compounds of the invention can be prepared from compounds and by the methods described in the following schemes.

Compounds of formula VI can be prepared from compounds of formula I as shown in Scheme 1.

Scheme 1

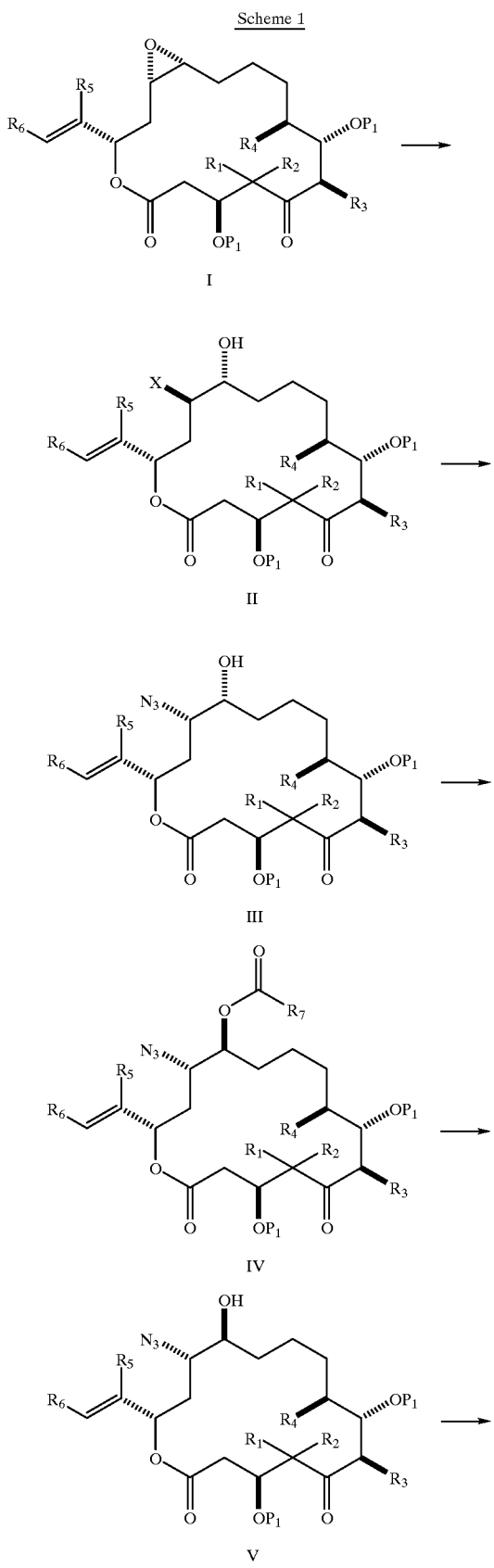

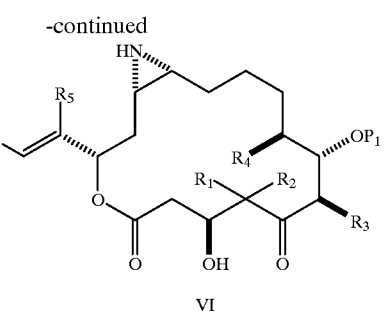

VI

The hydroxyl groups of formula I, where $P_1$ is hydrogen, $R_{1-5}$ are methyl and $R_6$ is 2-methyl-4-thiazolyl, can be optionally protected, for example, with triethylsilyl ethers, using methods known in the art. Other hydroxyl-protecting groups which are known in the art, and defined above as $P_1$, can also be used (see T. W. Greene and P. G. M. Wuts, *Protective Groups in Organic Synthesis*, John Wiley & Sons, Inc., New York, 1991). A compound of formula II, where X is a halogen, can be prepared from a compound of formula I by treatment with a metal halide salt, such as cesium halides, lithium halides, magnesium halides, and zinc halides, and including but not limited to, lithium bromide, magnesium bromide, zinc bromide, and zinc chloride. More preferably, the metal halide salt is magnesium bromide. A compound of formula III can be prepared from a compound of formula II by treatment with an azide salt such as lithium azide, sodium azide, tetraalkylammonium azide, or trialkylsilyl azide. Preferably the azide salt is sodium azide. A compound of formula IV, where $R_7$ is alkyl, substituted alkyl, aryl or substituted aryl, can be prepared from a compound of formula III by a Mitsunobu reaction (see 0. Mitsunobu and M. Yamada, *Bull. Chem. Soc. Japan* 40: 2380 (1967)) using triphenylphosphine, an azodicarboxylate, and a carboxylic acid such as 4-nitrobenzoic acid (see D. L. Hughes, *Organic Reactions*, Volume 42, Edited by L. Paquette et al., John Wiley & Sons, Inc., New York, 1992; and S. F. Martin and J. A. Dodge, *Tetrahedron Letters*, 3017 (1991)). A compound of formula V can be prepared from one of formula IV by hydrolysis or ammoniolysis of the ester group using, for example, a solution of ammonia in methanol. Other methods of ester cleavage, such as sodium hydroxide, potassium cyanide in methanol, and potassium carbonate in methanol, are well known in the art (see T. W. Greene and P. G. M. Wuts, *Protective Groups in Organic Synthesis*, John Wiley & Sons, Inc., New York, 1991, pp. 87–104). Optionally, a compound of formula V, where $P^1$ is a hydroxyl-protecting group can be deprotected using trifluoroacetic acid in dichloromethane, or other methods known in the art, such as hydrogen fluoride in acetonitrile, tetra-n-butylammonium fluoride, or acetic acid in THF/water. Hydroxyl-protecting groups may be alkanoyl, substituted alkanoyl, aroyl, substituted aroyl, trialkylsilyl, aryl dialkysilyl, diaryl alkylsilyl, or triarylsilyl. Preferably the hydroxyl-protecting group is trialkylsilyl, more preferably the protecting group is triethylsilyl. When $P_1$ is a protecting group other than triethylsilyl, deprotection methods known in the art can be used (see T. W. Greene and P. G. M. Wuts, *Protective Groups in Organic Synthesis*, John Wiley & Sons, Inc., New York, 1991, pp.10–142). Reduction of the azido group and subsequent cyclization of a compound of formula V with a reducing agent, such as a triarylor trialkylphosphine provides a compound of formula VI, where $R_{1-5}$ are methyl and $R_6$ is 2-methyl-4-thiazolyl.

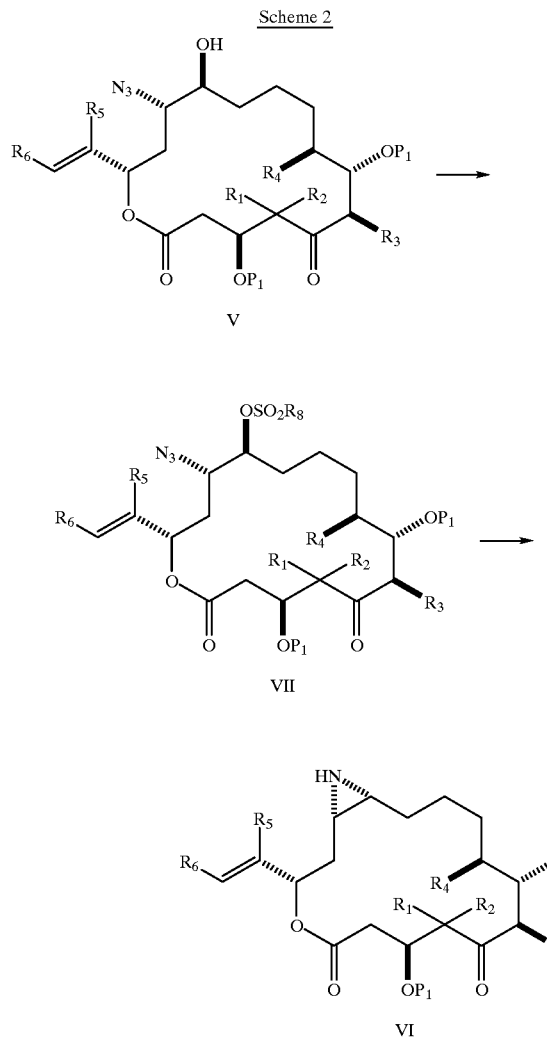

Alternatively, a compound of formula V, where $P_1$ is an hydroxyl-protecting group and $R_8$ is alkyl, substituted alkyl, aryl, or substituted aryl can be converted to an alkyl-, a substituted alkyl-, an aryl-, or a substituted arylsulfonate ester VII by treatment with an alkyl-, a substituted alkyl-, an aryl-, or a substituted arylsulfonyl chloride. Reduction of the azido group and subsequent cyclization of a compound of formula VII using a reducing agent such as a triaryl- or trialkylphosphine provides a compound of the invention such as formula VI (where $R_{1-5}$ are methyl and $R_6$ is 2-methyl-4-thiazolyl). Other azide reducing agents are well known in the art including, but not limited to, hydrogen, Lindlar's catalyst (Pd, $CaCO_3$/Pb), tri-n-butyltin hydride, stannous chloride, hydrogen sulfide, and 1,3-propanedithiol.

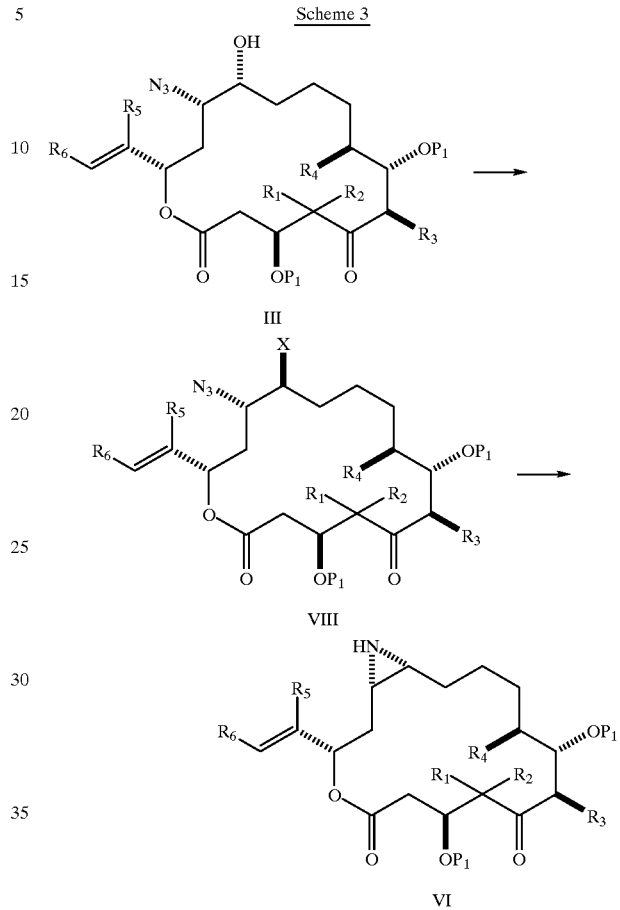

Alternatively, a compound of formula III where $P_1$ is a hydroxyl-protecting group, can be converted to a compound of formula VIII where X is a halogen by treatment with, for example, triphenylphosphine and a carbon tetrahalide. Alternative reagents for the conversion of a hydroxyl group to a halogen are well known in the art, such as thionyl chloride or phosphorous tribromide (see R. C. Larock, *Comprehensive Organic Transformations*, VCH Publishers, Inc., New York, 1989, pp. 352–359). Reduction of the azido group and subsequent cyclization of a compound of formula VIII using a reducing agent such as a triaryl- or trialkylphosphine provides a compound of the invention such as VI (where $R_{1-5}$ are methyl and $R_6$ is 2-methyl-4-thiazolyl). Other azide reducing agents are well known in the art including, but not limited to, hydrogen, Lindlar's catalyst (Pd, $CaCO_3$/Pb), tri-n-butyltin hydride, stannous chloride, hydrogen sulfide, and 1,3-propanedithiol.

EXAMPLE 1

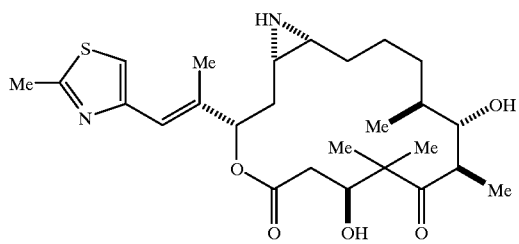

[1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-4-oxa-17-azabicyclo [14.1.0]heptadecane-5,9-dione A. [1S-[1R*,3R*(E),7R*,10S*,11R*,12R*,16S*]]-8,8,10, 12-Tetramethyl-3-[1-methyl-2-(2-methyl-4-thiazolyl) ethenyl]-7,11-bis[(triethylsily)oxy]-4,17-dioxabicyclo [14.1.0]heptadecane-5,9-dione.

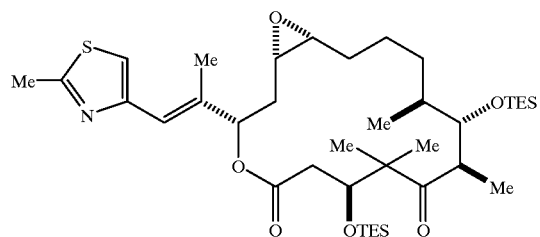

Et$_3$SiCl (25 ml, 149 mmol) was added to Epothilone A (10.39 g, 21 mmol), N,N-diisopropylethylamine (55 mL, 315 mmol), and imidazole (7.15 g, 105 mmol) in DMF (75 mL) at 25° C. The reaction mixture was heated at 55° C. for 6.5 hours and concentrated in vacuo. The residue was then diluted with CH$_2$Cl$_2$ (100 mL) and the organic extracts were washed with NaHCO$_3$ (30 mL), dried over Na$_2$SO$_4$ and concentrated in vacuo. The residue was purified by flash chromatography (SiO$_2$, 5.0×30 cm, hexanes to 15% EtOAc/hexanes gradient elution) to afford Compound A as a white solid (15.1 g, >95%). MS (ESI$^+$): (M+H)$^+$722.

B. [4S[-4R*,7S*,8R*,9R*,13S*,14S*,16R*(E)]]-14-Bromo-13-hydroxy-5,5,7,9-tetramethyl-16-[1-methyl-2-(2-methyl-4-thiazolyl)ethenyl]-4,8-bis[(triethylsilyl)oxy]-1-oxacyclohexadecane-2,6-dione.

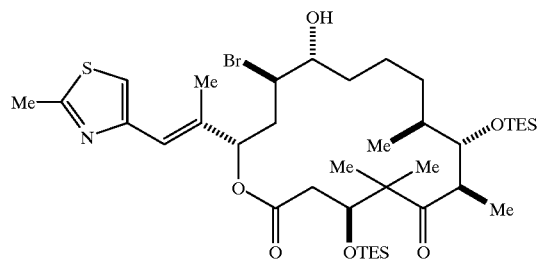

To a solution of Compound A from above (2.0 g, 2.8 mmol) in CH$_2$Cl$_2$ (30 mL) at −20° C. under argon was added MgBr$_2$·OEt$_2$ (3×1.1 g, 12 mmol total) in three portions every two hours while maintaining an internal temperature between −15 and −5° C. After 7 hours, the reaction mixture was quenched with pH 7 phosphate buffer (40 mL) and brine (40 mL), carefully extracted with EtOAc (3×100 mL), dried (Na$_2$SO$_4$), and concentrated in vacuo. The residue was purified by flash chromatography (SiO$_2$, 4.5×25 cm, 10–20% EtOAc/hexanes gradient elution) to afford Compound B as a white solid [1.0 g, 45% (67% based on 0.6 g of recovered starting material; <2% of the other C13—OH/C12—Br regioisomer was detected]. MS (ESI$^+$): (M+H)$^+$ 802.

C. [4S-[4R*,7S*,8R*,9R*,13S*,14R*,16R*(E)]]-14-Azido-13-hydroxy-5,5,7,9-tetramethyl-16-[1-methyl-2-(2-methyl-4-thiazolyl)ethenyl]-4,8-bis[(triethylsilyl)oxy]-1-oxacyclohexadecane-2,6-dione.

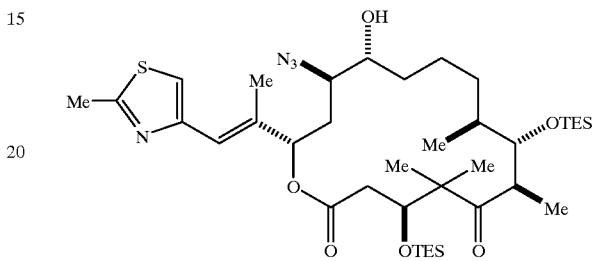

To a solution of Compound B from above (0.17 g, 0.21 mmol) in DMF (2 mL) under argon was added sodium azide (0.14 g, 2.1 mmol) and the resulting suspension was warmed to 43° C. After 36 hours, the solvent was removed in vacuo and the residue was directly purified by flash chromatography (SiO$_2$, 2.5×15 cm, 10–20% EtOAc/hexanes gradient elution) to give Compound C (0.14 g, 88%) as a white foam. MS (ESI$^+$): (M+H)$^+$765.

D. [4S-[4R*,7S*,8R*,9R*,13R*,14R*,16R*(E)]]-14-Azido-5,5,7,9-tetramethyl-16-[1-methyl-2-(2-methyl-4-thiazolyl)ethenyl]-13-[(4-nitrobenzoyl)oxy]-4,8-bis [(triethylsilyl)oxy]-1-oxacyclohexadecane-2,6-dione.

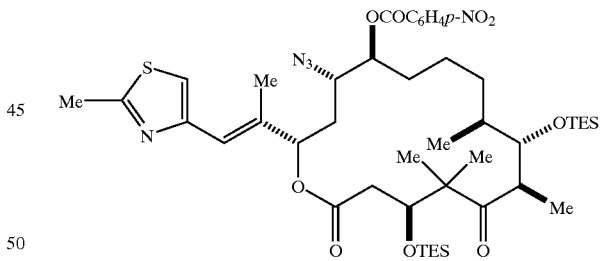

To a solution of Compound C from above (0.10 g, 0.13 mmol) in THF under argon was sequentially added 4-nitrobenzoic acid (55 mg, 0.33 mmol), triphenylphosphine (86 mg, 0.33 mmol), and diethyl azodicarboxylate (52 mL, 0.33 mmol). The reaction mixture was stirred at 25° C. for 1.5 hours, concentrated in vacuo and the residue was purified by flash chromatography (SiO$_2$, 2.5×10 cm, 10–20% EtOAc/hexanes gradient elution) to afford Compound D (0.10 g, 86%) as a white foam. MS (ESI$^+$): 914.6 (M+H)$^+$.

E. [4S-[4R*,7S*,8R*,9R*,13R*,14R*,16R*(E)]]-14-Azido-13-hydroxy-5,5,7,9-tetramethyl-16-[1-methyl-2-(2-methyl-4-thiazolyl)ethenyl]-4,8-bis [(triethylsilyl)oxy]-1-oxacyclohexadecane-2,6-dione.

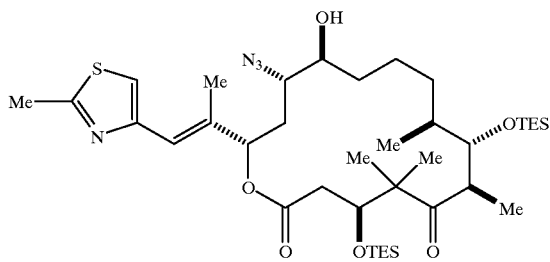

Compound D from above (0.10 g, 0.11 mmol) was treated with 2.0 M ammonia in methanol (1 mL) at 25° C. under argon for four hours. The solvent was removed in vacuo and the residue was directly purified by flash chromatography (SiO$_2$, 1.5×10 cm, 10–30% EtOAc/hexanes gradient elution) to afford Compound E (71 mg, 85%) as a white foam. MS (ESI$^+$): 765.5 (M+H)$^+$; MS (ESI$^-$): 763.3 (M−H)$^-$.

F. [4S-[4R*,7S*,8R*,9R*,13R*,14R*,16R*(E)]]-14-Azido-4,8,13-trihydroxy-5,5,7,9-tetramethyl-16-[1-methyl-2-(2-methyl-4-thiazolyl)ethenyl]-1-oxacyclohexadecane-2,6-dione.

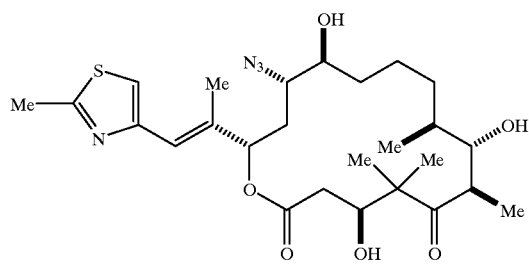

Compound E (15 mg, 20 mmol) was treated with 20% trifluoroacetic acid in methylene chloride (0.2 mL) at 0° C. under argon for ten minutes. The reaction mixture was concentrated under a constant stream of nitrogen at 0° C. and the residue was purified by flash chromatography (SiO$_2$, 1×5 cm, 0–5% MeOH/CHCl$_3$ gradient elution) to afford Compound F (9 mg, 86%) as a film. MS (ESI$^+$): 537.3 (M+H)$^+$.

G. [1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-4-oxa-17-azabicyclo[14.1.0]heptadecane-5,9-dione.

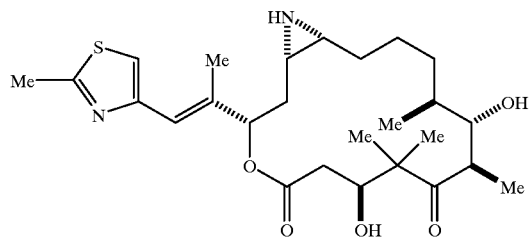

To a solution of Compound F (9 mg, 17 μmol) in THF (0.2 mL) under argon was added triphenylphosphine (18 mg, 67 μmol). The reaction mixture was warmed to 45° C. for four hours, and the solvent was removed under a constant flow of nitrogen. The residue was purified by radial chromatography (1 mm SiO$_2$ GF rotor, 2–10% MeOH—CHCl$_3$ gradient elution) to afford the title compound (4 mg, 50%) as a film.

Example 2

[1S-[1R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-4-oxa-17-azabicyclo[14.1.0]heptadecane-5,9-dione A. [4S-[4R*,7S*,8R*,9R*,13S*,14R*,16R*(E)]]-14-Azido-5,5,7,9-tetramethyl-16-[1-methyl-2-(2-methyl-4-thiazolyl)ethenyl]-13-[(methylsulfonyl)oxy]-4,8-bis[(triethylsilyl)oxy]-1-oxacyclohexadecane-2,6-dione.

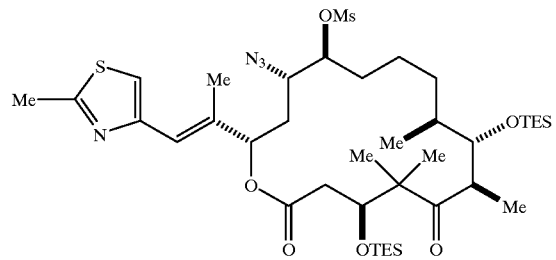

Compound 1E from above (1.047g, 1.37 mmol) was dissolved in CH$_2$Cl$_2$ (13 ml) and cooled at 0° C. Triethylamine (0.764 ml, 5.48 mmol) was added followed by methanesulfonylchloride (0.318 ml, 4.11 mmol) and the mixture was stirred at room temperature for three hours. The reaction was quenched with saturated aqueous NaHCO$_3$ (50 ml), the organic phase was extracted with CH$_2$Cl$_2$ (3×50 ml) and dried over Na$_2$SO$_4$ and concentrated in vacuo to afford compound 2A (1. 130 g, 98%), which was used in step 2B without further purification.

B. [1S-[1R*,3R*(E),7R*,10S*,11R*,12R*,16S*]]-8,8,10,12-Tetramethyl-3-[1-methyl-2-(2-methyl-4-thiazolyl)ethenyl]-7,11-bis[(triethylsilyl)oxy]-4-oxa-17-azabicyclo[14.1.0]heptadecane-5,9-dione.

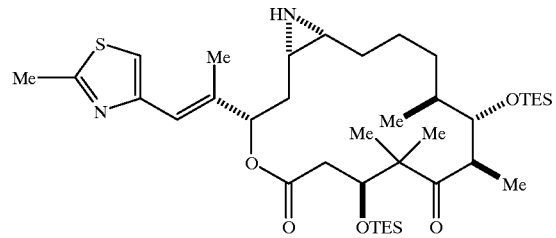

A solution of compound 2A from above (1.13 g, 1.34 mmol) was dissolved in tetrahydrofuran-H$_2$O (12:1, 24 mL) and treated with trimethylphosphine (2.68 ml, 1M in THF) at room temperature for three hours. Then the mixture was heated at 45° C. for 10 hours to convert the remaining aminomesylate into the aziridine. The volatiles were removed in vacuo and the residue was chromatographed (SiO$_2$, 50% ethyl acetate/Hexanes to 100% ethyl acetate) to afford compound 1B (0.82g, 85%).

C. [1S-[R*,3R*(E),7R*,10S*,11R*,12R*,16S*]]-7,11-Dihydroxy-8,8,10,12-tetramethyl-3-[1-methyl-2-(2-methyl-4-thiazolyl)ethenyl]-4-oxa-17-azabicyclo[14.1.0]heptadecane-5,9-dione.

19

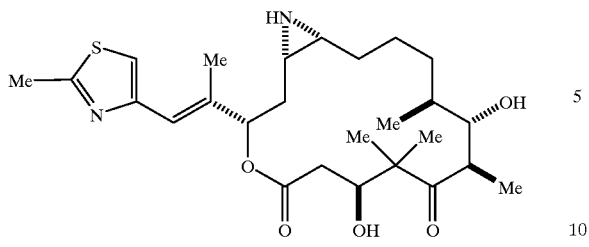

Compound 2B from above (3.44 g, 4.78 mmol) was dissolved in $CH_2Cl_2$ (25 ml), cooled to $-20°$ C. and treated with trifluoroacetic acid (20 ml, 10% in $CH_2Cl_2$). The reaction was slowly warmed up to 0° C. and after one hour was quenched with a saturated aqueous solution of $NaHCO_3$ (75 mL). The organic phase was extracted with ethyl acetate (3×100 mL) and $CHCl_3$ (100 mL), dried over $Na_2SO_4$ and concentrated in vacuo. The residue was purified by flash chromatography ($SiO_2$, $CHCl_3$ to 10%methanol/$CHCl_3$) to afford compound 2C (2.12 g, 90%).

What is claimed:

1. A process for preparing a compound of structure VI

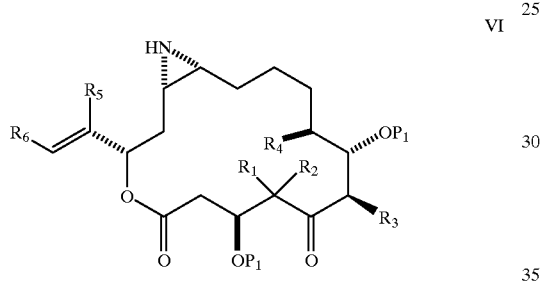

wherein:

$R_1$, $R_2$, $R_3$, $R_4$, $R_5$ are selected from the group H or alkyl and when $R_1$ and $R_2$ are alkyl can be joined to form a cycloalkyl;

$R_6$ is selected from the group consisting of H, alkyl, substituted alkyl, aryl, substituted aryl, cycloalkyl, or heterocyclo;

$R_7$ is selected from the group consisting of alkyl, substituted alkyl, aryl, or substituted aryl; and $P_1$ is selected from the group H, alkyl, substituted alkyl, alkanoyl, substituted alkanoyl, aroyl, substituted aroyl, trialkylsilyl, aryl dialkylsilyl, diaryl alkylsilyl, triarylsilyl;

which comprises:

(a) reacting a compound of structure I

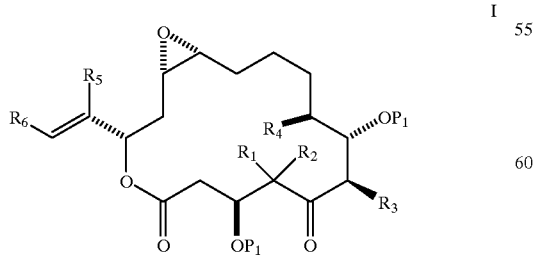

wherein $R_{1-6}$ and $P_1$ are defined as above with at least one metal halide salt to form structure II;

20

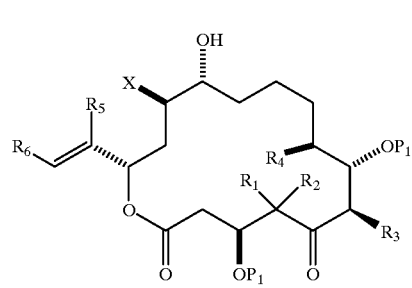

(b) reacting the product of (a) with at least one azide salt to form structure III;

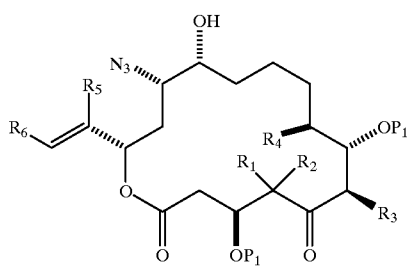

(c) conducting a Mitsunobu reaction with the product of (b) wherein $R_7$ is defined as above to form the structure IV;

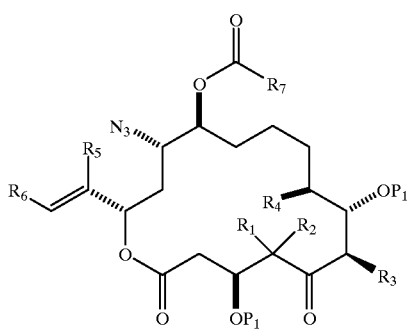

(d) cleaving the ester group of the product of (c) to form structure V;

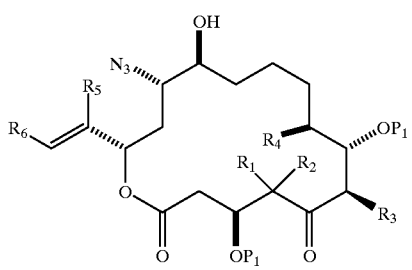

and (e) reducing and cyclizing the product of (d) with a reducing agent to form the stereospecific form of structure VI.

2. The process of claim 1 wherein the product of step (c) or (d) is deprotected prior to further reaction.

3. A compound of claim 1 having structure III:

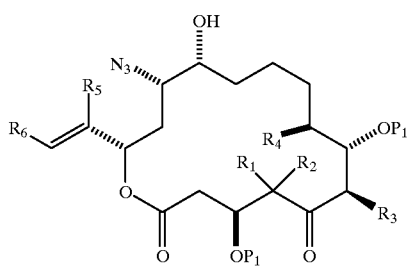

wherein $R_{1-6}$ and $P_1$ are defined therein.

4. A compound of claim 1 having structure IV:

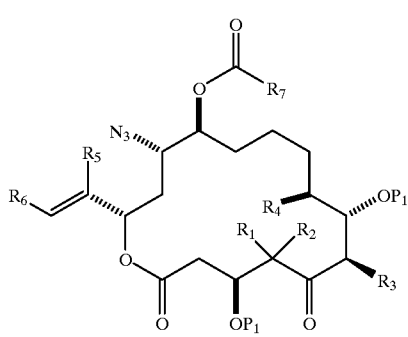

wherein $R_{1-7}$ and $P_1$ are defined therein.

5. A compound of claim 1 having structure V:

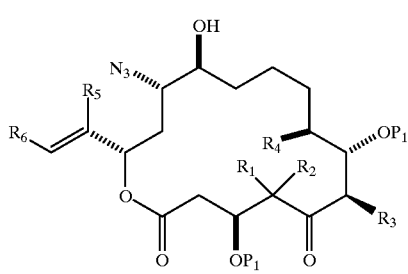

wherein $R_{1-6}$ and $P_1$ are defined therein.

6. A process for preparing a compound of structure VI

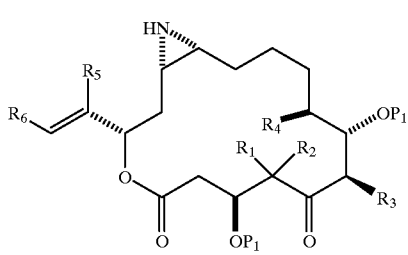

wherein:
$R_1$, $R_2$, $R_3$, $R_4$, $R_5$ are selected from the group H or alkyl and when $R_1$ and $R_2$ are alkyl can be joined to form a cycloalkyl;

$R_6$ is selected from the group consisting of H, alkyl, substituted alkyl, aryl, substituted aryl, cycloalkyl, or heterocyclo; and $P_1$ is selected from the group H, alkyl, substituted alkyl, alkanoyl, substituted alkanoyl, aroyl, substituted aroyl, trialkylsilyl, aryl dialkylsilyl, diaryl alkylsilyl, triarylsilyl;

which comprises:

(a) reacting a compound of structure V

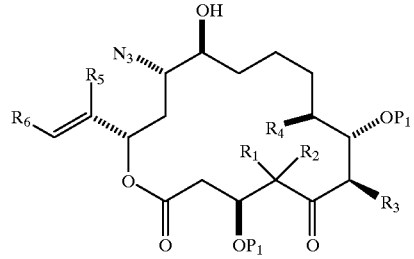

wherein $R_{1-6}$ and $P_1$ are defined as above with an alkyl-, a substituted alkyl-, an aryl-, or a substitued arylsulfonyl halide to form structure VII;

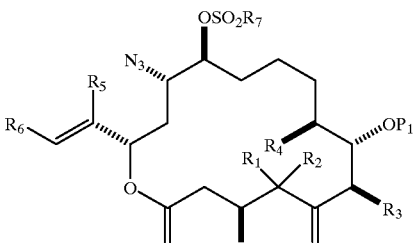

and (b) reducing and cyclizing the product of (a) wherein $R_7$ is an alkyl, substituted alkyl, aryl, or substitued aryl with a reducing agent to form the stereospecific form of structure VI.

7. A compound of claim 6 having structure VII:

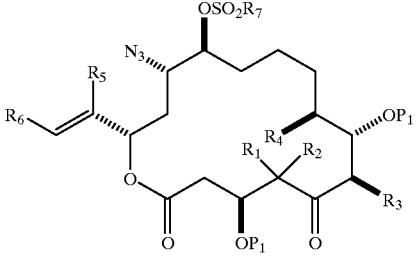

wherein $R_{1-7}$ and $P_1$ are defined therein.

8. A process for preparing a compound of structure VI

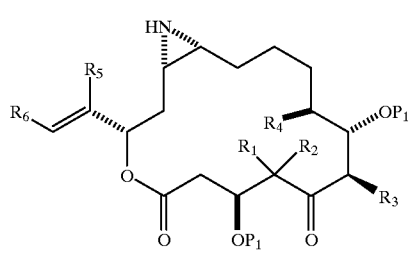

VI wherein:

$R_1$, $R_2$, $R_3$, $R_4$, $R_5$ are selected from the group H or alkyl and when $R_1$ and $R_2$ are alkyl can be joined to form a cycloalkyl;

$R_6$ is selected from the group consisting of H, alkyl, substituted alkyl, aryl, substituted aryl, cycloalkyl, or heterocyclo; and $P_1$ is selected from the group H, alkyl, substituted alkyl, alkanoyl, substituted alkanoyl, aroyl, substituted aroyl, trialkylsilyl, aryl dialkylsilyl, diaryl alkylsilyl, triarylsilyl;

which comprises:

(a) reacting a compound of structure III

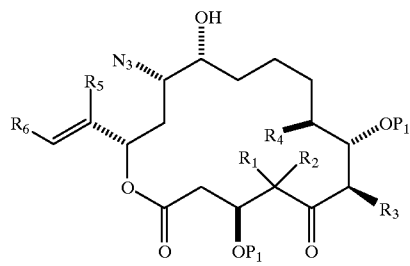

III wherein $R_{1-6}$ are defined above and $P_1$ is a protecting group with triphenylphosphine and a carbon tetrahalide to form structure VIII;

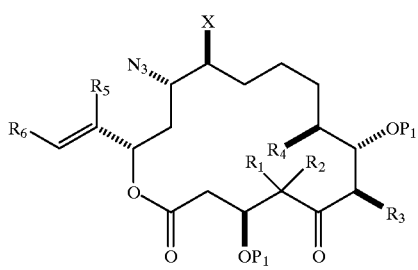

VIII and (b) reducing and cyclizing the product of (a) wherein X is a halogen with a reducing agent to form the stereospecific form of structure VI.

9. A compound of claim 8 having structure VIII:

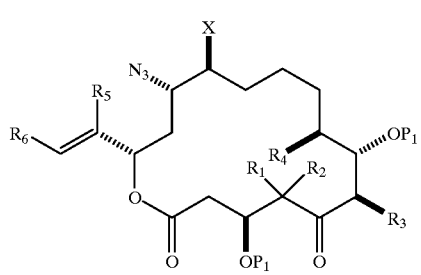

VIII wherein $R_{1-6}$ and $P_1$ are defined therein.

10. A process for preparing a compound comprising:

(a) reacting a compound of structure I

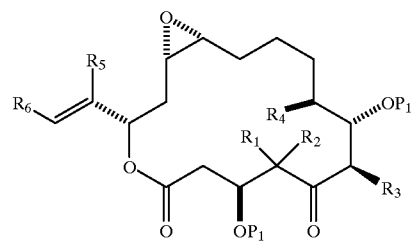

I wherein:

$R_1$, $R_2$, $R_3$, $R_4$, $R_5$ are selected from the group H or alkyl and when $R_1$ and $R_2$ are alkyl can be joined to form a cycloalkyl;

$R_6$ is selected from the group consisting of H, alkyl, substituted alkyl, aryl, substituted aryl, cycloalkyl, or heterocyclo;

$R_7$ is selected from the group consisting of alkyl, substituted alkyl, aryl, or substituted aryl; and $P_1$ is selected from the group H, alkyl, substituted alkyl, alkanoyl, substituted alkanoyl, aroyl, substituted aroyl, trialkylsilyl, aryl dialkylsilyl, diaryl alkylsilyl, triarylsilyl;

with at least one metal halide salt to form structure II;

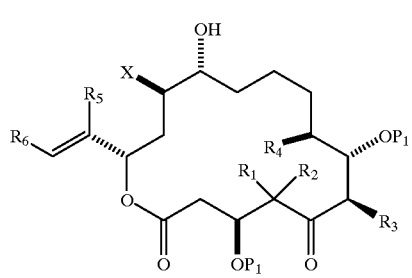

II (b) reacting the product of (a) with at least one azide salt to form structure III;

III
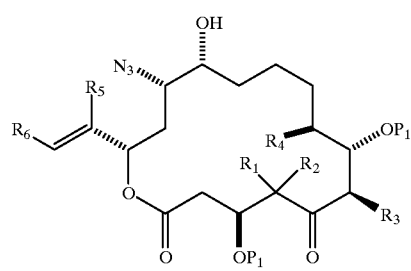
(c) conducting a Mitsunobu reaction with the product of (a) to form the structure
IV
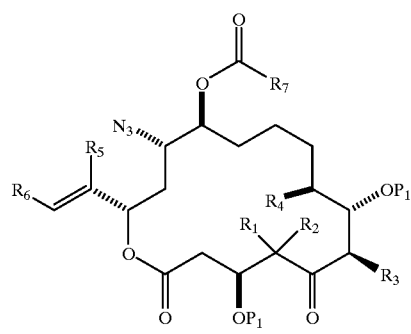
(d) cleaving the ester group of the product of (c) to form structure V;
V
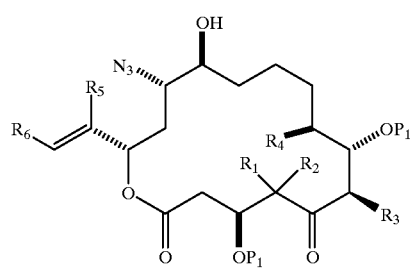
and
(e) reducing and cyclizing the product of (d) with a reducing agent to form the stereospecific form of structure VI.
VI
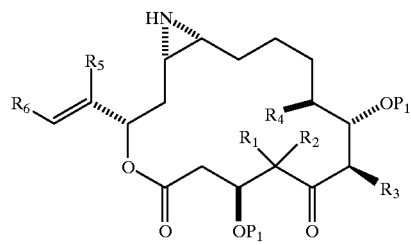
* * * * *